(12) United States Patent
Gow

(10) Patent No.: US 8,808,397 B2
(45) Date of Patent: Aug. 19, 2014

(54) PROSTHESES WITH MECHANICALLY OPERABLE DIGIT MEMBERS

(75) Inventor: David James Gow, Edinburgh (GB)

(73) Assignee: Touch Emas Limited, Livingston (GB)

( * ) Notice: Subject to any disclaimer, the term of this patent is extended or adjusted under 35 U.S.C. 154(b) by 1025 days.

(21) Appl. No.: 12/085,608

(22) PCT Filed: Jul. 16, 2006

(86) PCT No.: PCT/GB2006/002680
§ 371 (c)(1),
(2), (4) Date: Oct. 16, 2009

(87) PCT Pub. No.: WO2007/063266
PCT Pub. Date: Jun. 7, 2007

(65) Prior Publication Data
US 2010/0036507 A1   Feb. 11, 2010

(30) Foreign Application Priority Data

Nov. 29, 2005   (GB) .................................... 052484.7

(51) Int. Cl.
| | | |
|---|---|---|
| *A61F 2/54* | (2006.01) | |
| *A61F 2/68* | (2006.01) | |
| *A61F 2/66* | (2006.01) | |
| *A61F 2/58* | (2006.01) | |
| *A61F 2/30* | (2006.01) | |
| *A61F 2/50* | (2006.01) | |
| *A61F 2/72* | (2006.01) | |
| *A61F 2/76* | (2006.01) | |
| *A61F 2/70* | (2006.01) | |

(52) U.S. Cl.
CPC ....... *A61F 2/583* (2013.01); *A61F 2002/30527* (2013.01); *A61F 2002/30525* (2013.01); *A61F 2002/5073* (2013.01); *A61F 2002/30523* (2013.01); *A61F 2002/509* (2013.01); *A61F 2/72* (2013.01); *A61F 2220/0025* (2013.01); *A61F 2002/7655* (2013.01); *A61F 2002/701* (2013.01); *A61F 2/586* (2013.01); *A61F 2/68* (2013.01); *A61F 2002/5001* (2013.01); *A61F 2002/587* (2013.01)
USPC ............................................. 623/64; 623/57

(58) Field of Classification Search
CPC ....................................................... A61F 2/586
USPC ........................................................... 623/64
See application file for complete search history.

(56) References Cited

U.S. PATENT DOCUMENTS

| 2,592,842 A | 4/1952 | Alderson |
|---|---|---|
| 3,509,583 A | 5/1970 | Fraioli |

(Continued)

FOREIGN PATENT DOCUMENTS

| DE | 309367 | 11/1918 |
|---|---|---|
| DE | 198 54 762 | 6/2000 |

(Continued)

*Primary Examiner* — David Isabella
*Assistant Examiner* — Jacqueline Woznicki
(74) *Attorney, Agent, or Firm* — K&L Gates LLP

(57) ABSTRACT

A prosthesis (1) for providing at least one mechanically operable digit member. The prosthesis (1) has at least one digit member (3) extending generally tangentially with respect to a fixed worm gear wheel means (5) on a support member of the prosthesis and mounted for rotation about the worm gear wheel means axis (8). The digit member has a drive motor (7) operable to drive a worm means (13). The worm means (13) is in engagement with the worm gear wheel means (5) so that when the drive motor is operated, in use of the prosthesis, the digit member (3) moves around the worm gear wheel means (5), in which the worm means (13) is disposed outwith the digit member (3).

12 Claims, 2 Drawing Sheets

(56) References Cited

U.S. PATENT DOCUMENTS

| | | | |
|---|---|---|---|
| 3,683,423 A | | 8/1972 | Crapanzano |
| 3,837,010 A | * | 9/1974 | Prout ............................. 623/60 |
| 3,922,930 A | * | 12/1975 | Fletcher et al. ............. 74/665 B |
| 4,114,464 A | * | 9/1978 | Schubert et al. ............. 74/89.14 |
| 4,623,354 A | | 11/1986 | Childress et al. |
| 4,822,238 A | * | 4/1989 | Kwech .......................... 414/730 |
| 4,955,918 A | | 9/1990 | Lee |
| 5,062,673 A | * | 11/1991 | Mimura ........................ 294/111 |
| 5,888,246 A | * | 3/1999 | Gow ............................... 623/64 |
| 6,361,570 B1 | | 3/2002 | Gow |
| 6,660,043 B2 | * | 12/2003 | Kajitani et al. ................. 623/64 |
| 2005/0021154 A1 | * | 1/2005 | Brimalm ........................ 623/64 |
| 2005/0021155 A1 | | 1/2005 | Brimalm |
| 2008/0262634 A1 | * | 10/2008 | Puchhammer ................. 623/24 |

FOREIGN PATENT DOCUMENTS

| | | |
|---|---|---|
| GB | 1 510 298 | 5/1978 |
| WO | WO 95/24875 | 9/1995 |
| WO | WO 2007/063266 | 6/2007 |

\* cited by examiner

PROSTHESES WITH MECHANICALLY OPERABLE DIGIT MEMBERS

FIELD OF THE INVENTION

The present invention relates to prostheses having at least one mechanically operable digit member.

BACKGROUND TO THE INVENTION

Hand prostheses that provide one or more electromechanical wearer operable digits are known. Conventional prostheses often use an electric motor mounted in the hand itself and transmit motive power to the digits by means of a transmission system involving mechanical linkages. Such conventional prostheses have a number of shortcomings, notably a requirement for precise alignment between motor and transmission system, which can lead to a cumbersome arrangement, and the imposition of space requirements in the hand portion of the prosthesis, which can make the prosthesis unsuitable for a patient with some residual digits.

WO 95/24875 describes a hand prosthesis that addresses the above noted shortcomings of conventional prostheses. More specifically, the hand prosthesis of WO 95/24875 comprises a drive motor and gearbox mounted within a finger member. Operation of the drive motor drives a worm located within the finger member. The worm engages with and moves around a fixed worm gear wheel to move the finger member about the worm gear wheel axis.

The present inventor has appreciated certain shortcomings of the hand prostheses of WO 95/24875. More specifically, the size of the electromechanical components within the finger member makes it difficult to provide short prosthetic fingers with motors of sufficient power and with gears having appropriate ratios, such as are suitable for children.

It is therefore an aim of the present invention to provide a prosthesis having a digit member configured to provide for a small digit such as is suitable for children.

STATEMENT OF INVENTION

The present invention has been devised in the light of the above noted appreciation and thus from a first aspect there is provided a prosthesis for providing at least one mechanically operable digit member, the prosthesis having at least one said digit member extending generally tangentially with respect to a fixed worm gear wheel means on a support member of the prosthesis and mounted for rotation about the worm gear wheel means axis, the digit member having a drive motor operable to drive a worm means, the worm means being in engagement with the worm gear wheel means so that when the drive motor is operated, in use of the prosthesis, the digit member moves around the worm gear wheel means, characterised in that the worm means is disposed outwith the digit member.

Disposing the worm means outwith the digit member reduces the amount of longitudinal space taken up by electromechanical components within the digit member. This allows for the design of shorter digit members such as are suitable for children. In contrast, the hand prosthesis of WO 95/24875 has a worm means (i.e. the worm) disposed within the digit member as shown in FIG. 2 of WO 95/24875.

More specifically, the worm means may extend laterally to the digit member.

Alternatively or in addition, the worm means may extend substantially perpendicularly to the digit member.

Disposing the worm means in such a fashion allows for movement of the electo-mechanical components including the drive motor towards the worm gear wheel means.

Thus, alternatively or in addition, the worm means and the drive motor may be disposed on opposing sides of the worm gear wheel means axis.

In a form of the invention, the prosthesis may further comprise transmission means configured to couple movement of the drive motor to the worm means.

More specifically, the transmission means may be configured such that the axis of rotation of the worm means is inclined to the axis of rotation of the drive motor.

More specifically, the axis of rotation of the worm means may be inclined at about 90 degrees to the axis of rotation of the drive motor.

Alternatively or in addition, the transmission means may comprise first and second bevel gears that engage with each other, the first bevel gear being configured to move in response to movement of the drive motor and the second bevel gear being coupled to the worm means.

Alternatively or in addition, the worm gear wheel means has a profile that permits it to be disposed in relation to the digit member such that a distance between the worm gear wheel means axis and the digit member is less than a maximum radius of the worm gear wheel means. The maximum radius may be between the worm gear wheel means axis and a point on a peripheral edge of the worm wheel means which, in use, engages with the worm means.

This takes advantage of forms of the invention in which only a part of a peripheral edge of the worm gear wheel means engages with the worm means during use of the prosthesis. Thus, the worm gear wheel means can be located closer to the digit member than would be the case were the worm gear wheel means to have a circular profile, whereby a more compact prosthesis can be provided.

More specifically, the worm gear wheel means may have a profile that is roughly semi-circular.

More specifically, a curved peripheral edge of the semi-circle may be oriented for engagement with the worm means.

Alternatively or in addition, the digit member may be one of a finger member and a thumb member.

Alternatively or in addition, the worm means may comprise a worm.

Alternatively or in addition, the drive motor may be a permanent magnet DC motor having a substantially linear relation between torque and drive current.

Alternatively or in addition, the drive motor may be coupled by an output shaft thereof to a gearbox system whereby in use different torque—output drive speed ratios can be selected from a range of different ratios.

Alternatively or in addition, the prosthesis may have a plurality of digits each having at least one digit member and the prosthesis may be provided with control means configured to permit independence of movement of the digits or groups of digits.

More specifically, the plurality of digits may comprise a single thumb and at least one finger.

More specifically, the thumb may have a drive motor with high speed, low torque characteristics and the finger may have a drive motor with low speed, high torque characteristics.

Alternatively or in addition, the prosthesis may be clad with an overlay of aesthetically acceptable material having an appearance generally similar to a normal hand.

A further advantage of disposing the worm means outwith the digit member is that longitudinal space is freed up within the digit member.

Therefore, in another form of the invention the prosthesis may further comprise a further (second) digit member (e.g. a middle phalanx of a finger), the (first) digit member (e.g. a proximal phalanx of a finger) being coupled at its distal end to the further digit member to form a proximal joint allowing for movement of the further digit member in relation to the digit member.

Provision of the proximal joint in the prosthesis takes advantage of the longitudinal space freed up within the digit member.

More specifically, the prosthesis may be configured for powered actuation of the proximal joint.

Alternatively or in addition, the prosthesis may be configured such that the further digit member is movable in relation to the digit member in a first direction by powered actuation.

More specifically, the prosthesis may be configured such that the further digit member is movable in relation to the digit member in a second opposing direction by biasing means.

Thus, the biasing means can return the further digit member to its position in relation to the digit member before powered actuation.

More specifically, the biasing means may comprise spring means, such as a helical spring.

Alternatively or in addition, the prosthesis may be configured such that the proximal joint is actuated by operation of the drive motor.

More specifically, the prosthesis may further comprise proximal joint transmission means configured to couple movement of the drive motor to the further digit member and thereby actuate the proximal joint.

More specifically, the proximal joint transmission means may comprise a proximal joint transmission member attached at a first end to the worm gear wheel means and attached at a second, opposing end to the further digit member.

More specifically, the first end of the proximal joint transmission member may be attached to the worm gear wheel means at a location spaced apart from the worm gear wheel means axis.

Thus, movement of the digit member around the worm gear wheel means when the drive motor is operated may cause a distance between the location of attachment of the joint transmission member on the gear wheel means and a location towards the end of the digit member to increase. Accordingly where the proximal joint transmission member is inextensible the movement of the digit member around the worm gear wheel means may cause the joint transmission member to move the further digit member towards the gear wheel means and relative to the digit member about the proximal joint.

More specifically, the joint transmission member may comprise a pliable member of predetermined length.

More specifically, the prosthesis may be configured such that the predetermined length of the pliable member may be changed.

Alternatively or in addition, the pliable member may comprise a plurality of teeth spaced apart along the pliable member for engaging with a corresponding profile on and thereby providing attachment to at least one of the worm gear wheel means and the further digit member.

More specifically, a portion of the plurality of teeth on the pliable member may engage with the corresponding profile, whereby a length of the pliable member may be changed by changing those teeth engaging with the corresponding profile.

The present inventor has realised that the feature of the proximal joint between the digit member and the further digit member is of wider application than hitherto described.

Thus according to a second aspect of the present invention there is provided a prosthesis for providing at least one mechanically operable digit, the prosthesis having at least one said digit comprising a drive motor and first (e.g. a proximal phalanx) and second (e.g. middle phalanx) digit members, the first digit member being coupled at its proximal end to a support member of the prosthesis to form a first joint (e.g. a metacarpophalangeal [MCP] joint) allowing for motion of the first digit member in relation to the support member and the first digit member being coupled at its distal end to the second digit member to form a second joint (e.g. a proximal intermediate phalangeal [PIP] joint) allowing for motion of the second digit member in relation to the first digit member, the first digit member and support member being configured such that when the drive motor is operated the first joint is actuated, in which the prosthesis is configured for powered actuation of the second joint.

More specifically, the prosthesis may be configured such that the second digit member is movable in relation to the first digit member in a first direction by powered actuation.

More specifically, the prosthesis may be configured such that the second digit member is movable in relation to the first member in a second opposing direction by biasing means.

Thus, the biasing means can return the second digit member to its position in relation to the first digit member before powered actuation.

More specifically, the biasing means may comprise spring means, such as a helical spring.

Alternatively or in addition, the prosthesis may be configured such that the second joint is actuated by operation of the drive motor.

More specifically, the prosthesis may further comprise proximal joint transmission means configured to couple movement of the drive motor to the second digit member and thereby actuate the second joint.

In a form of the second aspect of the present invention, the prosthesis may comprise gear means having first and second gear components in engagement with each other, the first gear component being configured to move in response to movement of the drive motor and the second gear component being coupled to the support member of the prosthesis, so that when the drive motor is operated, in use of the prosthesis, the gear means is operable to cause rotation of the first digit member in relation to the support member.

More specifically, the first gear component may be disposed outwith the digit member.

Alternatively or in addition, the gear means may comprise a worm-gear with the first component comprising a worm and the second component comprising a worm gear wheel.

More specifically, the proximal joint transmission means may comprise a proximal joint transmission member attached at a first end to the worm gear wheel and attached at a second, opposing end to the second digit member.

More specifically, the first end of the proximal joint transmission member may be attached to the worm gear wheel at a location spaced apart from the worm gear wheel means axis.

Thus, movement of the first digit member around the worm gear wheel when the drive motor is operated may cause a distance between the location of attachment of the joint transmission member on the gear wheel and a location towards the end of the first digit member to increase. Accordingly where the proximal joint transmission member is inextensible the movement of the first digit member around the worm gear wheel may cause the joint transmission member to move the second digit member towards the gear wheel and relative to the first digit member about the second joint.

More specifically, the joint transmission member may comprise a pliable member of predetermined length.

More specifically, the prosthesis may be configured such that the predetermined length of the pliable member may be changed.

Alternatively or in addition, the pliable member may comprise a plurality of teeth spaced apart along the pliable member for engaging with a corresponding profile on and thereby providing attachment to at least one of the worm gear wheel and the second digit member.

More specifically, a portion of the plurality of teeth on the pliable member may engage with the corresponding profile, whereby a length of the pliable member may be changed by changing those teeth engaging with the corresponding profile.

Further embodiments of the second aspect of the present invention may comprise one or more features of the first aspect of the present invention.

According to a further aspect of the present invention, there is provided a prosthesis for providing at least one mechanically operable digit member, the prosthesis comprising: at least one said digit member having a drive motor; and gear means having first and second gear components in engagement with each other, the first gear component being coupled to the drive motor and the second gear component being coupled to a support member of the prosthesis, so that when the drive motor is operated, in use of the prosthesis, the gear means is operable to cause rotation of the digit member in relation to the support member, in which the first gear component is disposed outwith the digit member.

More specifically, the gear means may comprise a worm-gear with the first component comprising a worm and the second component comprising a worm gear wheel.

Further embodiments of the further aspect of the present invention may comprise one or more features of the first aspect of the present invention.

References herein to digits are to generally complete digits, such as a finger, a thumb or even a toe, and references to digit members are to components of complete digits, such as the proximal phalanx, middle phalanx and distal phalanx of the finger, or combinations of such components, such as the middle phalanx and distal phalanx.

BRIEF DESCRIPTION OF DRAWINGS

Further features and advantages of the present invention will become apparent from the following specific description, which is given by way of example only and with reference to the accompanying drawings, in which.

SPECIFIC DESCRIPTION

Figure 1:
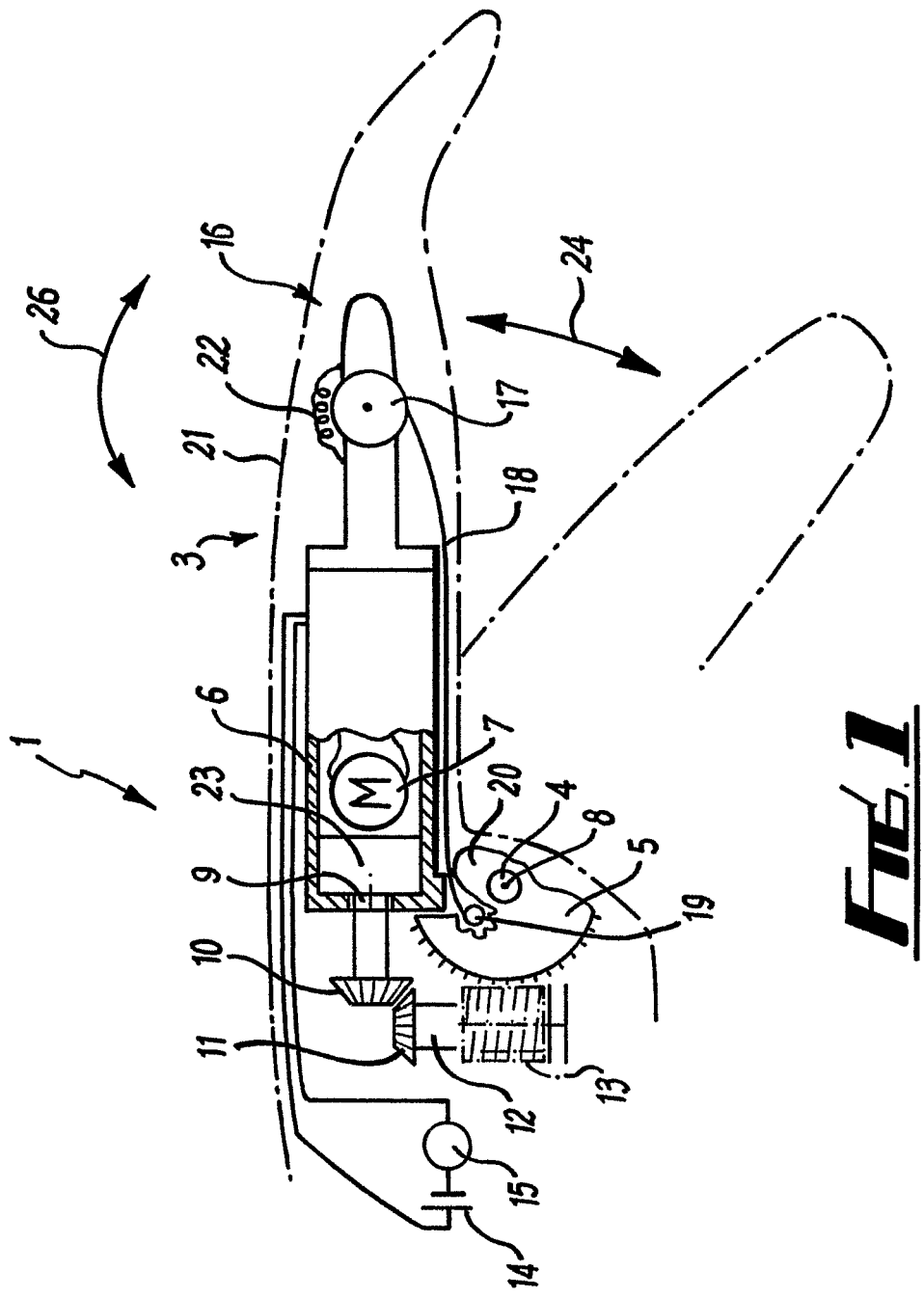
FIG. 1 is a partly cut-away view of a finger member of the prosthesis according to the present invention.

FIG. 1 shows a partly cut-away view of a hand prosthesis 1 having a finger 3 (which constitutes a digit). The prosthesis 1 is securely fixed in use to a patient's hand stump (not shown) in a generally known manner by means of a main body (not shown). The main body has a spindle 4 on which a worm gear wheel 5 is fixedly mounted. Worm gear wheel 5 is of roughly semi-circular profile. Finger 3 extends generally tangentially with respect to worm gear wheel 5. Finger 3 has a generally tubular housing 6, in which is mounted a drive motor 7 having a gearbox system 23. The gearbox system 23 provides for different torque—output drive speed ratios to be selected from a range of different ratios. Lugs (not shown) depend from the underside of the tubular housing 6 and are rotatably mounted on the spindle to allow for rotation of the finger 3 in relation to the spindle 4 and worm gear wheel 5. The centre 8 of the spindle 4 defines an axis (which constitutes a worm gear wheel means axis) about which the finger 3 rotates. The housing 6 containing the drive motor 7 corresponds to the proximal phalanx of a finger and the joint formed between the spindle 4 and the lugs depending from the housing 6 correspond to the metacarpophalangeal (MCP) or knuckle joint of a finger.

A drive shaft 9 extends from the drive motor 7 and gearbox system 23. A first bevel gear 10 is mounted on the distal end of the drive shaft 9. A second bevel gear 11 is mounted within the prosthesis 1 such that an axis of rotation of the second bevel gear 11 is at substantially 90 degrees to an axis of rotation of the first bevel gear 10. First and second bevel gears 10, 11 together constitute transmission means. The gear ratio of the first and second bevel gears 10, 11 is substantially 1 to 1, although the gear ratio can be readily changed by known means. The second bevel gear 12 is mounted on the same shaft 12 as a worm 13. The worm 13 is located such that it engages with a toothed curved peripheral edge of worm gear wheel 5. As can be seen from FIG. 1 the worm 13 extends laterally to the housing 6 at an angle of about 90 degrees.

It should be noted that the worm 13 is located in the prosthesis such that it is outside the housing 6 (which corresponds to a digit member). Thus, the worm is located within the hand of the prosthesis and not the finger 3 even though the prosthesis is structured such that the worm 13 moves with the housing 6 upon operation of the finger 3, as described below.

The drive motor 7 is a permanent magnet DC motor having a substantially linear relation between torque and drive current. Furthermore, the drive motor is powered by small rechargeable batteries 14, which may be mounted remotely of the prosthesis. The drive motor is controlled by means of switches 15 (which constitutes control means), which are actuated by known means, e.g. residual digit movement or wrist movement. Alternatively or in addition, control may be by means of pressure sensitive resistors or signals derived from the electromyographic activity of residual muscle actions. In forms of the invention in which the prosthesis comprises a plurality of other digits, i.e. a thumb and one or more other fingers, control by known means provides for independence of movement of the digits or groups of digits. In the case of a finger the drive motor 7 has low speed, high torque characteristics and in the case of a thumb the drive motor has high speed. Low torque characteristics.

Finger 3 has a finger tip portion 16 corresponding to the middle and distal phalanges of a finger (and which constitutes a second digit member), which forms with the distal end of the housing 6 a proximal joint 17 corresponding to a proximal intermediate phalangeal (PIP) joint of a finger. Arrow 24 represents movement of the finger 3 about axis 8 (i.e. the MCP joint) and arrow 26 represents movement of finger tip portion 16 about PIP joint 17.

A toothed inextensible belt 18 is attached at a first end to the worm gear wheel 5 in an aperture 19 provided in the worm gear wheel 5, passes over a protrusion 20 formed on the worm gear wheel and is attached at a second end to the finger tip portion 16. A helical spring 22 (which constitutes a biasing means) is connected at one end to the end of housing 6 and at a second opposing end to the finger tip portion 16.

The prosthesis is clad with an overlay 21 of silicone rubber or the like to provide an aesthetically acceptable appearance as similar as practicable to a normal hand appearance in a known manner.

Figure 2:
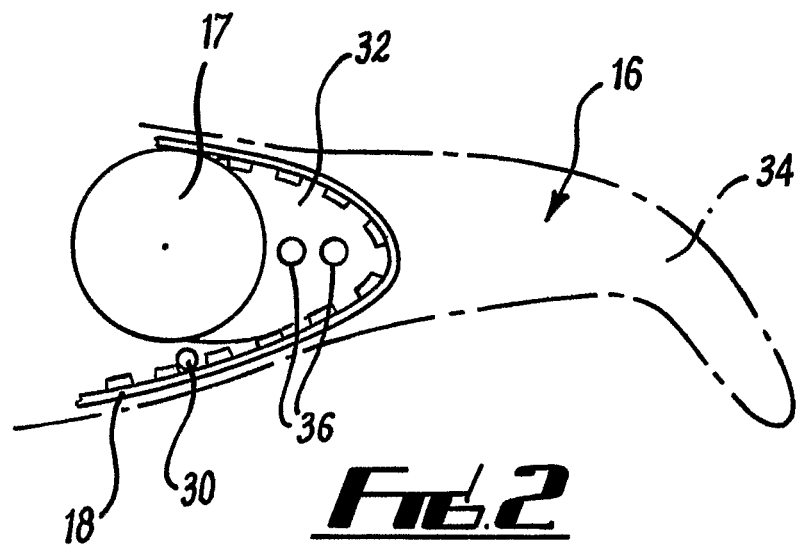
FIG. 2 is a detailed view of the Proximal Intermediate Phalangeal (PIP) joint of FIG. 1.

FIG. 2 is a detailed view of the PIP joint 17 of FIG. 1. As with FIG. 1 the finger tip portion 16 corresponds to the middle and distal phalanges of a finger. As can be seen from FIG. 2, the toothed belt 18 passes over a roller 30 mounted near the joint 17 before passing over a finger tip core 32, which is a solid body formed from a plastics or metal and attached to the joint 17. Finger tip core 32 has indentations formed in its surface that are shaped to receive the teeth on the belt 18 and provide for engagement between finger tip core 32 and the belt 18. The effective length of the belt 18 can be adjusted by a graduated amount corresponding to the spacing of the teeth on the belt by disengaging the belt 18 from the finger tip core 32 and moving the belt in the requisite direction before re-engaging belt and finger tip core. When the belt has been engaged as required a cover 34 is located over the distal portion of the finger and secured by means of screws 36 to sandwich the belt 18 between the cover 34 and the finger tip core 32.

Figure 3:
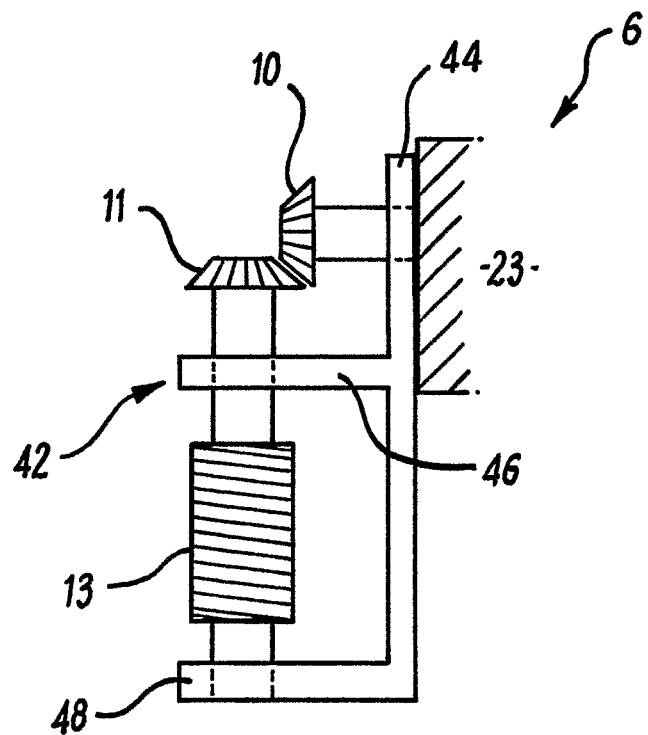
FIG. 3 is a detailed view of the bevel gear arrangement of the prosthesis of FIG. 1.

FIG. 3 provides a detailed view of the bevel gears of the prosthesis. The prosthesis comprises a bevel support member 42 having three limbs 44, 46, 48, with second and third limbs 46, 48 disposed perpendicularly to the first limb 44, thereby forming a double l-shape in profile, with the worm 13 disposed between the second and third limbs 46, 48. As shown in FIG. 3 the first limb 44 is attached to the housing 6 of the prosthesis. The shaft of the first bevel gear 10 passes through an aperture provide in the first limb 44 of the bevel support member 42 and the shaft of the second bevel gear 11 passes through an aperture provided in the second limb 46 of the bevel support member. Also, a shaft of the worm 13 is received in a recess provided in the third limb 48. Thus, the l-shaped bevel support member supports the first and second bevel gears 10, 11 and the worm 13 and provides for ease of relative location of the first and second bevel gears 10, 11 during assembly of the prosthesis. In an un-illustrated alternative form, the bevel support member 42 has a large single limb instead of the second and third limbs 46, 48 shown in FIG. 3. The large single limb of the alternative form of bevel support member 42 defines a bore in which the worm 13 is supported. In addition, the large single limb is formed such that it supports the shaft of the second bevel gear 11 and the shaft of the worm 13 in much the same fashion as shown in and described with reference to FIG. 3.

In use the wearer actuates the finger by means of the control means described above, which provides for operation of the drive motor 7. Operation of drive motor 7 causes rotation of the first bevel gear 10, which rotates the second bevel gear 11 along with the worm 13. As worm 13 rotates it progresses around the peripheral surface of fixed worm gear wheel 5 either clockwise or anti-clockwise depending on the direction of rotation of drive motor 7. This moves the finger 3 about axis 8 as indicated by arrow 24. As finger 3 moves about axis 8 in a downward direction the distance between the point of attachment of toothed belt 18 in aperture 19 of the worm gear wheel 5 and the proximal joint 17 reduces. This is because aperture 19 is offset from the axis of the worm gear wheel as shown in FIG. 1. As the distance reduces the fixed length toothed belt 18 pulls on the finger tip portion 16 against the bias of the helical spring 22 to rotate the finger tip portion 16 clockwise in relation to the rest of the finger 3. Upon reversal of the direction of rotation of the finger 3 about the axis, i.e. movement of finger 3 upwards, tension is released on the toothed belt 18 and the spring 22 exerts a bias on the finger tip portion 16 to return the finger tip portion to the extended position shown in FIG. 1.

The invention claimed is:

1. A prosthesis for providing a mechanically operable digit, the prosthesis comprising:
   a worm gear wheel mounted to a support member of the prosthesis, the worm gear wheel being adjacent to the digit;
   the mechanically operable digit comprising a drive motor within a motor housing, the digit being mounted for rotation about the worm gear wheel; and
   a worm gear operatively coupled to the drive motor and in engagement with the worm gear wheel so that when the drive motor is operated, in use of the prosthesis, the digit rotates around the worm gear wheel and rotates in relation to the support member, wherein the worm gear is disposed outside the motor housing; and
   a transmission configured to couple the drive motor to the worm,
   wherein an axis of rotation of the worm gear is oriented at 90° to an axis of rotation of the drive motor.

2. A prosthesis including a mechanically operable digit, the prosthesis comprising:
   a fixed worm gear wheel mounted to a support member of the prosthesis, the fixed worm gear wheel having an axis of rotation adjacent to the digit;
   the mechanically operable digit including a longitudinal axis extending generally tangentially with respect to the fixed worm gear wheel, wherein the digit comprises a drive motor having a motor housing and a motor shaft extending from the motor housing having a longitudinal axis parallel to the longitudinal axis of the digit and having a beveled gear located at one end of the shaft; and
   a worm gear having a shaft having a longitudinal axis around which the worm gear rotates, the worm gear being in engagement with the worm gear wheel, the worm gear shaft having a beveled gear located at one end, the worm gear being located outside the digit;
   wherein the drive motor is operable to rotate both the worm gear and the digit around the worm gear wheel,
   wherein the longitudinal axis of the worm gear shaft is substantially oriented at 90° to the longitudinal axis of the motor shaft, and
   wherein the beveled gear of the worm gear shaft and the beveled gear of the motor shaft are in rotatable engagement.

3. A prosthesis according to claim 2 in which the worm gear wheel has a profile that permits it to be disposed in relation to the digit such that a distance between a worm gear wheel axis and the digit is less than a maximum radius of the worm gear wheel.

4. A prosthesis according to claim 2 in which the worm gear wheel has a profile that is roughly semi-circular.

5. A prosthesis according to claim 2 in which the drive motor is a permanent magnet DC motor having a substantially linear relation between torque and drive current.

6. A prosthesis according to claim 2 in which the drive motor shaft is coupled to a gearbox system whereby in use different torque-output drive speed ratios can be selected from a range of different ratios.

7. A prosthesis according to claim 2 in which the prosthesis has a plurality of digits, each of the plurality of digits includes a respective drive motor and wherein the prosthesis includes a controller configured to permit independence of movement of the plurality of digits.

8. A prosthesis according to claim 7 in which the plurality of digits comprises a single thumb and at least one finger, the thumb having a drive motor with higher speed, lower torque characteristics and the finger having a drive motor with lower speed, higher torque characteristics.

9. The prosthesis of claim 2 wherein the mechanically operable digit further comprises a distal end comprising a second rotatable joint proximal to the tip of the mechanically operable digit and distal to the axis of rotation of the mechanical digit about the fixed worm gear wheel, the second rotatable joint being rotated by movement of the digit about the fixed worm gear wheel.

10. The prosthesis of claim 9 wherein the rotation of the second joint by movement of the digit about the fixed worm gear is caused by a line attached to the tip of the mechanically operable digit and the worm gear wheel.

11. A prosthesis comprising:
- a fixed worm gear wheel mounted to a support member of the prosthesis, the fixed worm gear wheel having an axis of rotation adjacent to a mechanically operated digit;
- the mechanically operable digit having at least a first joint proximate a tip of the mechanically operable digit;
- a main body operatively coupled to the mechanically operable digit;
- a drive motor located within a motor housing located within the mechanically operable digit;
- a worm gear located adjacent to the mechanically operable digit and external to the motor housing, the worm gear operatively coupled to the drive motor to reorient the mechanically operable digit with respect to the fixed worm gear wheel,
- wherein the worm includes a rotation axis that is orthogonal to a rotational axis of the drive motor.

12. The prosthesis of claim 11, further comprising beveled gears operatively coupled between the drive motor and the worm.

* * * * *